United States Patent [19]

Navarrini et al.

[11] Patent Number: 5,296,617

[45] Date of Patent: Mar. 22, 1994

[54] PROCESS FOR PREPARING 1,3-DIOXOLES

[75] Inventors: Walter Navarrini; Simonetta Fontana, both of Milan, Italy

[73] Assignee: Ausimont S.p.A., Milan, Italy

[21] Appl. No.: 831,169

[22] Filed: Feb. 5, 1992

[30] Foreign Application Priority Data

Feb. 7, 1991 [IT] Italy .................. MI 91 A 000320

[51] Int. Cl.$^5$ ........................................... C07D 317/42
[52] U.S. Cl. ...................................................... 549/455
[58] Field of Search ........................................ 549/455

[56] References Cited

U.S. PATENT DOCUMENTS

| | | | |
|---|---|---|---|
| 3,865,845 | 2/1975 | Resnick | 549/455 |
| 4,393,227 | 7/1983 | Squire | 549/455 |
| 4,485,250 | 11/1984 | Squire | 549/455 |
| 4,908,461 | 3/1990 | Hung | 549/455 |

FOREIGN PATENT DOCUMENTS

| | | |
|---|---|---|
| 0460948 | 12/1991 | European Pat. Off. . |
| 9103472 | 3/1991 | PCT Int'l Appl. . |
| 1361346 | 7/1974 | United Kingdom . |
| 2211845 | 7/1989 | United Kingdom . |

OTHER PUBLICATIONS

Hohorst et al., "Some Reactions of Bis(fluoroxy)difluoromethane, $CF_2(OF_2)_2$", Inorganic Chemistry, vol. 7, No. 3, pp. 624–626 (Mar. 1968).

Primary Examiner—C. Warren Ivy
Assistant Examiner—A. A. Owens
Attorney, Agent, or Firm—Bryan Cave

[57] ABSTRACT

A process for preparing 1,3-dioxoles of formula:

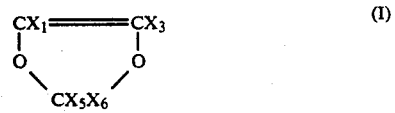

in which $X_1$ and $X_3$, like or different from each other, are F or H, $X_5$ and $X_6$, like or different from each other, are F or $CF_3$, by dehalogenation reaction of the corresponding 4,5-dihalodioxolanes in the presence of a dehalogenation agent at a temperature ranging from +30° to +130° C.

The starting dioxolanes are essentially in the isomeric form anti.

10 Claims, No Drawings

PROCESS FOR PREPARING 1,3-DIOXOLES

The present invention relates to a process for preparing 1,3-dioxoles by dehalogenation of the corresponding 4,5-dihalodioxolanes.

More in particular, the present invention relates to a process for preparing fluorinated 1,3-dioxoles having formula:

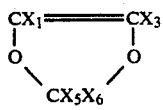

in which:
$X_1$ and $X_3$, like or different from each other, are F or H,
$X_5$ and $X_6$, like or different from each other, are F or $CF_3$.

The growing demand for fluorodioxoles for the use thereof as monomers in the preparation of fluoropolymers justifies the interest in perfecting the processes for preparing them.

It is known how to prepare dioxoles by dehalogenation of 4,5-dihalo-1,3-dioxolanes in the presence of a metal such as magnesium or zinc.

U.S. Pat. Nos. 3,865,845 and 3,978,030 describe a process for the dehalogenation of fluorinated dioxolanes in an organic solvent in the presence of magnesium with a yield of 58% by mols. Furthermore, there is illustrated the debromination reaction with metallic zinc of perfluoro-2,2-dimethyl-4,5-dibromo-1,3-dioxolane, prepared by treating perfluoro-2,2-dimethyl-1,3-dioxole with bromine, in order to obtain the starting dioxole with a yield of 18% by mols. The yields of this process, besides being low, are little reproduceable.

U.S. Pat. No. 4,393,227 describes an improved dechlorination process with magnesium, mercury metal or a mercury salt, iodine and tetrahydrofuran, by means of which the reproduceability of the yields is improved. However, the drawback of this process is that the molar ratios of the metals to one another must be exact and defined, since even slight variations result in a drastic reduction in the dioxole yield.

Lastly, U.S. Pat. No. 4,908,461 describes a method of dechlorinating 1,3-dioxolanes in the presence of $LiAlH_4$ and $TiCl_3$ or $TiCl_4$ in tetrahydrofuran. However, the utilized methodology is quite complex and the molar ratios of the dehalogenating agents to each other and to the starting dioxolane must be within defined ranges.

From an examination of the prior art it results that there is the need for having available an easy industrial process which permits to prepare 1,3-dioxoles through dehalogenation of the corresponding 4,5-dihalodioxolanes with high yields and a high reproduceability.

So far, any efforts have been essentially directed to the improvement of the dehalogenating agent.

It has now surprisingly found by the Applicant that, irrespectively of the utilized dehalogenating agent, the dehalogenation reaction of 4,5-dihalodioxolanes exhibits high yields when the two halogen atoms, which are extracted, are in anti position.

Thus, it is an object of the present invention to provide a process for preparing dioxoles of formula:

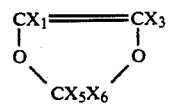

wherein:
$X_1$ and $X_3$, like or different from each other, are F or H,
$X_5$ and $X_6$, like or different from each other, are F or $CF_3$, which comprises the following steps of:
a) preparing a dioxolane of formula:

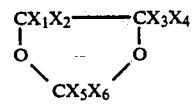

wherein:
$X_2$ and $X_4$, like or different from each other, are Cl or Br,
$X_1$, $X_3$, $X_5$ and $X_6$ have the same meaning as defined before, starting from reagents in which the halogens $X_2$ and $X_4$ are substantially in trans position, or by means of a process such that the anti/syn isomeric ratio in the resulting dioxolane is higher than the trans/cis isomeric ratio of the starting reagents;
b) reacting said dioxolane with at least a dehalogenating agent;
c) subsequently separating the dioxole (I) from the reaction products of step b).

The reaction of step b) is conducted at a temperature ranging from $+30°$ to $+130°$ C., preferably from $+50°$ to $+100°$ C.

It has now surprisingly been found that, if the preparation of dioxolane (II) as per step a) is effected according to the process described in European patent appln. (EP 460,948) in the name of the Applicant, said dioxolane exhibits an anti/sun isomeric ratio, which is higher than the trans/cis ratio of the starting reagents.

According to this process, dioxolane (II) is obtained from the reaction of a bis(fluoroxy)perfluoroalkane of formula $C(OF)_2X_5X_6$ with a halogenated olefin of formula $CX_1X_2=CX_3X_4$, where $X_1$, $X_2$, $X_3$, $X_4$, $X_5$ and $X_6$ have the meaning defined hereinbefore.

The temperature of said reaction is generally in a range from $-140°$ to $+60°$ C., preferably from $-100°$ to $+30°$ C.

All the characteristics of the above reaction are contained in the above-cited Eur. Pat. application No. 460,948.

More particularly, EP 460,948 relates to the preparation of halogenated 1,3-dioxolanes having formula:

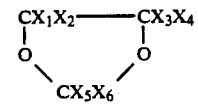

wherein: $X_1$, $X_2$, $X_3$, and $X_4$, like or different from one another, represent F, Cl, Br, I, $CF_2OSO_2F$, $SO_2F$, $C(O)F$, H, perhaloalkyl or oxyperhaloalkyl radicals containing from 1 to 5 carbon atoms, and $X_5$ and $X_6$, like or different from each other, represent F or $CF_3$.

It is an object of EP 460,948 to provide a single-stage process for preparing 1,3-dioxolanes of formula (III), which does not exhibit the limitations and the drawbacks affecting the processes of the prior art. Another object of EP 460,948 is to provide new halogenated 1,3-dioxolanes. Thus, an object of the EP 460,948 is a process for preparing halogenated 1,3-dioxolanes of formula (III) wherein: $X_1$, $X_2$, $X_3$, and $X_4$, like or different form one another, represent F, Cl, Br, I, $CF_2OSO_2F$, $SO_2F$, $C(O)F$, H, perhaloalkyl or oxyperhaloalkyl radicals containing from 1 to 5 carbon atoms, and $X_5$ and $X_6$, like or different from each other, represent F or $CF_3$, characterized in that a bis(fluoroxy)perfluoroalkane of formula $C(OF)_2X_5X_6$ is reacted, at a temperature ranging from $-140°$ to $+60°$ C., with a halogenated olefin of formula $CX_1X_2=CX_3X_4,X_1$, $X_2$, $X_3$, $X_4$, $X_5$ and $X_6$ being the same as defined hereinabove.

In a preferred embodiment of EP 460,948, a flow of a bis(fluoroxy)perfluoroalkane, preferably in the presence of an inert diluting gas, and optionally also a gaseous or liquid stream consisting of a halogenated olefin, are fed into a liquid phase consisting of a halogenated olefin and of a solvent, if any, maintained at the above-cited reaction temperature. As an alternative, the halogenated olefin and the bis(fluoroxy)perfluoroalkane are simultaneously fed into a vessel containing optional solvent. At the end of the reaction time, feeding of the reagents is stopped and the reaction products are separated from the solvent, if any, and from the unreacted olefin, if present, preferably by fractionated distillation. The reaction can be conducted also in a thoroughly continuous manner by continuously withdrawing a liquid phase portion from the reactor, from this phase the reaction products are separated and recovered, while the optional solvent and the unreacted olefin are recycled. The total pressure in the reaction environment preferably ranges from 1 to 10 kg/cm² abs. More usually, it is operated at about atmospheric pressure. The inert diluting gas of bis(fluoroxy)perfluoroalkane when it is utilized, is selected for example from nitrogen, argon, helium, $CF_4$ and $C_2F_6$.

A further embodiment of EP 460,948 is a particular discontinuous process for preparing halogenated 1,3-dioxolanes of formula (III), wherein:

$X_1$, $X_2$, $X_3$, and $X_4$, like or different from one another, represent F, Cl, Br, I, $CF_2OSO_2F$, $SO_2F$, $C(O)F$, H, perhaloalkyl 2 or oxyperhaloalkyl radicals containing from 1 to 5 carbon atoms, and $X_5$ and $X_6$ like or different from one another, represent F or $CF_3$, characterized in that a bis(fluoroxy)perfluoroalkane of formula $C(OF)_2X_5X_6$ is reacted, at a temperature ranging from $-140°$ C. to $+60°$ C., with a halogenated olefin of formula $CX_1X_2=CX_3X_4,X_1$, $X_2$, $X_3$, $X_4$, $X_5$ and $X_6$ being the same as defined hereinbefore, on condition that at least one from among $X_1$, $X_2$, $X_3$ and $X_4$ is F. In the discontinuous method the reagents are condensed at a temperature not exceeding $-140°$ C. in the reaction vessel, preferably along with a solvent. The abovesaid condensation is preferably conducted at a temperature of $-196°$ C. The reaction vessel so charged is usually allowed to reach the desired reaction temperature and is maintained at this temperature for a time from 1 hour to 24 hours. The reaction products are purified by vacuum distillation by causing the vapors to flow through cooled traps. It must be pointed out that the temperature at which the reagents are condensed in the reaction vessel is not the actual reaction temperature, but only a convenient experimental procedure for charging the reagents in a discontinuous and exact manner without letting them react or to minimize any reaction until the desired reaction temperature is reached. In the discontinuous method the pressure preferably ranges from 0.5 to 20 kg/cm² abs. In both processes the reaction can be conducted in a condensed phase or in a gas phase.

The synthesis of bis(fluoroxy)perfluoroalkanes of formula:

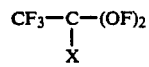

wherein X is F or $CF_3$, is described in JACS (1967), 2263 and in U.S. Pat. No. 3,420,866. Among the utilized bis(fluoroxy)perfluoroalkanes, bis(fluoroxy) difluoromethane (BDM) is particularly preferred. The synthesis of BDM is described in JACS (1967), 1809–10. The halogenated olefins utilized in EP 460,948 preferably contain from 2 to 6 carbon atoms. Particularly preferred olefins are, for example: $CFCl=CFCl$, $CFBr=CFBr$, $CF_2=CFBr$, $CF_2=CH-CF_3$, $CF_2=CF-SO_2F$, $CF_2=CF-CF_2-OSO_2F$, $CF_2=CF-C(O)F$, $CF_2=CF-CF_3$, $CF_2=CF-O-CF_2-CF_3$. The reaction temperature for both processes is usually in the range from $-140°$ to $+60°$ C.; preferably it ranges from $-100°$ to $+30°$ C. The solvent, when it is utilized, is preferably selected from straight and cyclic fluorocarbons, chlorofluorocarbons, perfluoroamines and perfluorinated ethers. Examples of suitable fluorocarbons and chlorofluorocarbons are: perfluorocyclobutane, perfluorocyclohexane, 1-chloropentafluoroethane, 1,1,2-trichloro-1,2,2-trifluoroethane, 1,2-dichlorotetrafluoroethane and 1,1,1-trifluorotrichloroethane. Examples of suitable perfluoroamines are the perfluoroaminic FLUORINERT produced by 3M Co. Examples of suitable perfluorinated ethers are the perfluoropolyethers having a boiling point lower than 250° C., such as the GALDEN produced by Montefluos. The halogenated olefin concentration in the liquid phase generally ranges from 0.01 to 10 moles/liter and above, i.e., up to the molar concentrations of the haloolefins in the pure state.

A further object of EP 460,948 are new 1,3-dioxolanes of formula (III), wherein: $X_1$, $X_2$, $X_3$ and $X_4$, like or different from one another, represent F, Cl, Br, I, $CF_2OSO_2F$, $SO_2F$, $C(O)F$, H, perhaloalkyl or oxyperhaloalkyl radicals containing from 1 to 5 carbon atoms, $X_5$ and $X_6$, like or different from each other, represent F or $CF_3$, on condition that at least one from among $X_1$, $X_2$, $X_3$ and $X_4$ is Br, I, $CF_2OSO_2F$, $SO_2F$, $C(O)F$, a perhaloalkyl or oxyperhaloalkyl radical containing from 1 to 5 carbon atoms and furthermore that, when one from among $X_1$, $X_2$, $X_3$ and $X_4$ is $CF_3$, at least one among the other three is different from F, or $X_5$ and $X_6$ are $CF_3$, and when one from among $X_1$, $X_2$, $X_3$ and $X_4$ is Br or I, the other three are F, or at least one among $X_5$ and $X_6$ is F. The abovesaid 1,3-dioxolanes are preparable according to the process of EP 460,948 by reacting, at a temperature ranging from $-140°$ C. to $+60°$ C., a bis(fluoroxy)perfluoroalkane of formula $C(OF)_2X_5X_6$ with a halogenated olefin of formula $CX_1X_2=CX_3X_4$, where for $X_1$, $X_2$, $X_3$, $X_4$, $X_5$ and $X_6$ the above-listed conditions are valid. The starting halogenated olefin formula $CX_1X_2=CX_3X_4$ preferably contains at least two, and more preferably at least three F atoms among the substituents $X_1$, $X_2$, $X_3$ and $X_4$. Furthermore, in the starting bis(fluoroxy)perfluoroalkane of formula $C(OF)_2X_5X_6$, and $X_5X_6$ are preferably F. The resulting 1,3-dioxolanes can be utilized as fluorinated fluids, for example as an alternative to the chlorofluorocarbons available on the market. They are also used as general anesthetics.

Using said process, the proportion of anti isomer in the dioxolane is usually of at least 60% and more commonly of at least 80%.

Preferably, the ratio between trans isomer and cis isomer in the starting halogenated olefin is of at least 1:1.

In the dioxolanes of formula (II), $X_1$, $X_3$, $X_5$ and $X_6$ are preferably F.

Particularly preferred are 4,5-dichloro-tetrafluoro-1,3-dioxolane and 4,5-dibromo-tetrafluoro-1,3-dioxolane.

Starting from the abovesaid preferred dioxolanes, the obtained product is perfluoro-1,3-dioxole.

As concerns the dehalogenation reaction as per step b), the dehalogenating agent/dioxolane molar ratio can vary over a relatively wide range. Usually it is higher than 1, preferably it ranges from 1.5 to 3.0.

The dehalogenating agent is selected from the ones of the art. Preferably, it is a metal selected from the class comprising Zn, Mg, Hg, Cu, Fe, Sn. Particularly preferred is zinc.

In a preferred embodiment, the starting dioxolane is fed to the reaction vessel maintained at the reaction temperature, which vessel contains the dehalogenating agent along with an optional solvent and, preferably, with little amounts of sodium or potassium iodide and of sodium or potassium carbonate (usually up to about 1% by weight in respect of the dehalogenating agent).

On conclusion of the reaction, the reaction products are collected in a trap maintained at a lower temperature than the boiling temperature of said products.

In order to favour this operation, a gaseous nitrogen flow should be preferably provided in the reaction vessel.

The solvent, if it is used, shall be inert under the reaction conditions, and it is preferably selected from amides (such as dimethylformamide), ethers (such as dioxane) and sulphoxides (such as dimethylsulphoxide).

Usually it is operated at about atmospheric pressure. However, it is possible to use both reduced pressures and pressures higher than 1 atmosphere.

The reaction time is not a critical parameter; usually the reaction is concluded in a few minutes.

The resulting dioxoles can be utilized as monomers for preparing copolymers and homopolymers, as is described e.g. in published European application No. 80,187 and in U.S. Pat. Nos. 4,535,175 and 3,978,030.

The abovesaid polymers are utilizable, e.g., as anticorrosive coating material or as sheaths for optical fibres.

For purposes of promoting a better understanding of the possibilities of carrying out the present invention, illustrative examples are given hereunder; it will nevertheless be understood that no limitation of the scope of the invention is thereby intended.

EXAMPLE 1

Preparation of 4,5-dichloro-tetrafluoro-1,3-dioxolane

Into a 5-neck glass reactor having a 100 ml volume, maintained at a temperature of $-78°$ C., equipped with mechanical stirrer, reflux cooler, thermocouple and inner plunging pipe for letting in the gases, there were introduced 10 g of 1,2-dichloroperfluoro-ethylene (mixture of 50% cis and 50% trans) and 75 ml of dichlorodifluoromethane, maintaining the reactor at a temperature of $-65°$ C.

To the reactor so charged and maintained at a temperature of $-65°$ C. there were fed 0.851 liters of bis(fluoroxy) difluoromethane (BDM), at a flowrate of 0.4 l/h, diluted with $N_2$ (0.5 l/h).

From the reaction rough product, after stripping of most of the solvent, the reaction products were separated by fractionated distillation in a tray column at atmospheric pressure. The fraction with boiling point at 47° C. consisting of 7.25 g of 4,5-dichloro-tetrafluoro-1,3-dioxolane with a purity degree of 99.2% was collected; the impurity consisted of 1,1,2-trichloro-1,2,2-trifluoroethane.

The isolated dioxolane was composed of a mixture of syn isomer (20%) and anti isomer (80%).

The reaction by-product 1,2-dichlorotetrafluoroethane formed in an equimolar amount with respect to the dioxolane and was prevailingly collected in the distillation fraction having a boiling point in the range of from 3° C. to 4° C.

The distillation column contained 800 mg of $CF_2Cl$ $CFClCFCl$ $CF_2Cl$.

The dioxolane yield, defined as the ratio between mols of obtained dioxolane and mols of utilized BDM, was of 88%.

EXAMPLE 2

Preparation of 4,5-dichloro-tetrafluoro-1,3-dioxolane

To a multineck glass reactor having a 50 ml volume, equipped with a magnetic entrainment mechanical stirrer, reflux cooler, thermocouple, inner plunging pipe, and immersed in a bath cooled at $-80°$ C., there were fed—after having introduced 35.3 g of 1,2-dichloro-1,2-difluoroethylene (mixture of 50% cis and 50% trans)—0.6 l of bis(fluoroxy)difluoromethane at a flowrate of 0.4 l/h, diluted with $N_2$ (0.5 l/h).

The reaction rough product was distilled in a Spaltrohr-Fisher tray column at atmospheric pressure, thereby obtaining the following products: 2.3 g of $CF_2Cl$—$CF_2Cl$, 28.3 g of $CFCl$=$CFCl$, 4.5 g of 4,5-dichloro-tetrafluoro-1,3-dioxolane and 2.1 g of $CF_2Cl(CFCl)_2CF_2Cl$.

The isolated dioxolane was composed of a mixture of syn (20%) and anti (80%) isomers.

The dioxolane yield, calculated as in example 1, was of 78%.

EXAMPLE 3

Preparation of 4,5-dibromo-tetrafluoro-1,3-dioxolane

Into a multineck glass reactor having a 100 ml volume, equipped with magnetic entrainment mechanical stirrer, reflux cooler, thermocouple, inner plunging pipe, immersed in a bath cooled at $-80°$ C., there were introduced 75 ml of $CF_2Cl_2$ and 10 g of 1,2-dibromo-1,2-difluoroethylene (mixture of 22% cis and 78% trans).

To the reactor so charged and maintained at a temperature of $-80°$ C., 0.5 l of bis(fluoroxy)difluoromethane diluted with $N_2$ (0.5 l/h) were fed at a flowrate of 0.4 l/h.

On conclusion of the reaction, after having distilled off the solvent, there were recovered 12.2 g of a mixture consisting of: $CF_2Br_2$ (3.8%), $CF_2BrCF_2Br$ (37.8%), 4,5-dibromotetrafluoro-1,3-dioxolane (49.4%) and $CFBr_2CF_2Br$ (8.8%); said mixture was analyzed by means of gas chromatography in a column sp. 1000 at a temperature gradient from 50° C. up to 200° C. (10° C./min.). From such mixture, distilled in a Spaltrohr-Fisher tray column at atmospheric pressure, 5.4 g of a dioxolane having a boiling point from 69° to 72° C. were recovered.

The dioxolane was composed of a mixture of syn (10%) and anti (90%) isomers.

The dioxolane yield, defined as in example 1, was of 79.6%.

EXAMPLE 4

Dehalogenation of 4,5-dichloro-tetrafluoro-1,3-dioxolane

Operating in a nitrogen atmosphere, Zn (4.4 g), KI (180 mg), $K_2CO_3$ (300 mg) and dimethylformamide (DMF) (7 ml) were introduced into a 50 ml flask, equipped with thermometer, dropping funnel, distillation column and magnetic stirrer.

Then, after having brought the mixture to 60° C., there were dropped thereinto, very slowly (1 hour), 2.75 g of 4,5-dichloro-tetrafluoro-1,3-dioxolane (synthesized according to the method described in example 1) dissolved in 2.5 ml of DMF. During dropping, the mixture was heated up to 100° C. and perfluoro-1,3-dioxole was removed by distillation as it formed.

In the collection flask there were condensed 1.76 g of a distillate which, analyzed by means of gas chromatography (column sp. 1000, from 50° C. to 180° C., 10° C./min.), resulted to be composed of: perfluoro-1,3-dioxole (82.2%), 4-chloro-2,2,4,5-tetrafluoro-1,3-dioxolane (3%) and 4,5-dichloro-2,2,4,5-tetrafluoro-1,3-dioxolane (15%).

The mixture was then distilled in a conventional vacuum line through four traps respectively cooled at −80° C., −130° C., −150° C. and −196° C.

1,370 g of perfluoro-1,3-dioxole were collected in the trap cooled at −150° C.

The isolated perfluoro-1,3-dioxole yield, calculated on the converted dioxolane, was of 82%.

EXAMPLE 5

The preceding example was repeated following the same modalities and using the same ratio between the reagents, with the only exception that the mixture of isomers of 4,5-dichloro-2,2,4,5-tetrafluoro-1,3-dioxolane (2.3 g) was composed for 86.3% of anti isomer and for 13.7% of syn isomer.

From the mixture collected during the reaction there were recovered by successive distillation, as in example 1, 1.250 g of perfluoro-1,3-dioxole and 110 mg of unreacted 4,5-dichloro-2,2,4,5-tetrafluoro-1,3-dioxolane.

The perfluoro-1,3-dioxole yield, calculated as in example 1, was of 85%.

EXAMPLE 6

The preceding example was repeated, using 2 g of a mixture of isomers of 4,5-dichloro-2,2,4,5-tetrafluoro-1,3-dioxolane, which mixture was composed for 65% of anti isomer and for 35% of syn isomer.

842 mg of perfluoro-1,3-dioxole and 150 mg of unreacted 4,5-dichloro-2,2,4,5-tetrafluoro-1,3-dioxolane were recovered from the reaction. The perfluoro-1,3-dioxole yield, calculated as in the preceding examples, was of 68%.

We claim:

1. A process for preparing 1,3-dioxoles of formula:

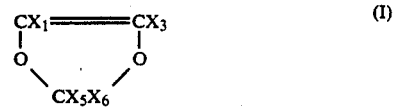

wherein:
$X_1$ and $X_3$, like or different from each other, are F or H,
$X_5$ and $X_6$, like or different from each other, are F or $CF_3$,
which comprises the steps of:
a) preparing a dioxolane of formula:

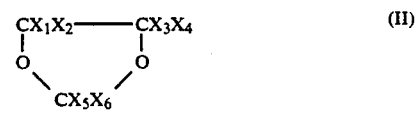

wherein:
$X_2$ and $X_4$, like or different from each other, are Cl or Br,
$X_1$, $X_3$, $X_5$ and $X_6$ have the meaning defined hereinbefore, starting from reagents in which the halogens $X_2$ and $X_4$ are substantially in trans position, or by a process such that the anti/syn isomeric ratio in the resulting dioxolane is higher than the trans/cis isomeric ratio of the starting reagents;
b) reacting said dioxolane with at least a dehalogenating agent at a temperature ranging from +30° to +130° C.;
c) separating the dioxol (I) from the reaction product of step b).

2. The process of claim 1, characterized in that the dioxolane (II) is obtained from the reaction of a bis(-fluoroxy)perfluoroalkane of formula $C(OF)_2X_5X_6$ with a halogenated olefin of formula $CX_1X_2=CX_3X_4$ at a temperature ranging from −140° to +60° C., $X_1$, $X_2$, $X_3$, $X_4$, $X_5$ and $X_6$ having the meaning defined hereinbefore.

3. The process of claim 1, characterized in that the reaction of the dioxolane with at least a dehalogenating agent is conducted at a temperature ranging from +50° to +100° C.

4. The process of claim 1, characterized in that the dehalogenating agent is a metal selected from the class comprising Zn, Mg, Hg, Cu, Fe and Sn.

5. The process of claim 4, characterized in that the dehalogenating agent is metallic Zn.

6. The process of claim 1, characterized in that the reaction of the dioxolane with at least a dehalogenating agent is conducted in the presence of sodium or potassium iodide and of sodium or potassium carbonate.

7. The process of claim 1, characterized in that the reaction of the dioxolane with at least a dehalogenating agent is conducted in a solvent, which is inert under the reaction conditions.

8. The process of claim 7, characterized in that the solvent is selected from amides, ethers and sulphoxides.

9. The process of claim 1, characterized in that $X_1$ and $X_3$ are F.

10. The process of claim 1, characterized in that $X_5$ and $X_6$ are F.

* * * * *